United States Patent

Hayashi et al.

Patent Number: 5,231,202
Date of Patent: Jul. 27, 1993

[54] OPTICALLY ACTIVE TERTIARY PHOSPHINE COMPOUND AND TRANSITION METAL COMPLEX USING THE SAME AS LIGAND

[75] Inventors: Tamio Hayashi; Yasuhiro Uozumi; Akiko Yamazaki, all of Hokkaido; Hidenori Kumobayashi, Tokyo, all of Japan

[73] Assignee: Takasago International Corporation, Tokyo, Japan

[21] Appl. No.: 850,998

[22] Filed: Mar. 12, 1992

[30] Foreign Application Priority Data

Mar. 12, 1991 [JP] Japan .................. 3-070339
Sep. 19, 1991 [JP] Japan .................. 3-266864

[51] Int. Cl.[5] .......................... C07F 15/00; C07F 9/02
[52] U.S. Cl. ..................... 556/21; 556/136; 568/17
[58] Field of Search ............... 556/21, 136; 568/17

[56] References Cited

U.S. PATENT DOCUMENTS

4,604,474 8/1986 Kumobayashi et al. ........... 556/7
4,691,037 9/1987 Yoshikawa et al. ............... 556/18

FOREIGN PATENT DOCUMENTS

55-61937 5/1980 Japan .

OTHER PUBLICATIONS

Journal of the American Chemical Society, vol. 113, pp. 9887–9888 (1991).
Chemistry Express, vol. 6, No. 5, pp. 335–338 (1991).

Primary Examiner—José G. Dees
Assistant Examiner—Porfirio Nazario
Attorney, Agent, or Firm—Sughrue, Mion, Zinn, Macpeak & Seas

[57] ABSTRACT

A phosphine compound represented by formula (I):

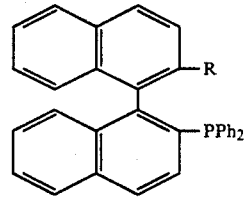

(I)

wherein Ph represents a phenyl group; and R represents a lower alkyl group or $-OR^1$, wherein $R^1$ represents a hydrogen atom, a cycloalkyl group having from 5 to 7 carbon atoms, or an alkyl group having from 1 to 6 carbon atoms which may be substituted with a halogen atom, a lower alkoxy group, a lower alkoxy group-substituted lower alkoxy group, or a phenyl group, and a transition metal complex using the phosphine compound (I) as a ligand are disclosed. The transition metal complex, when used as a catalyst for various enantioselective synthesis reactions, e.g., enantioselective silylation reaction, provides a desired product in high yield at high optical purity. The absolute configuration of the product can be arbitrarily selected by selecting the optical isomer of the ligand in the transition metal complex catalyst.

10 Claims, No Drawings

OPTICALLY ACTIVE TERTIARY PHOSPHINE COMPOUND AND TRANSITION METAL COMPLEX USING THE SAME AS LIGAND

FILED OF THE INVENTION

This invention relates to a novel phosphine compound and, more particularly, to a phosphine compound which provides a complex with a transition metal, e.g., ruthenium, palladium, and rhodium, the complex being useful as a catalyst for various enantioselective synthesis reactions.

BACKGROUND OF THE INVENTION

A good number of reports have been made on transition metal complexes useful for enantioselective synthesis reactions such as enantioselective hydrogenation, enantioselective isomerization, and enantioselective silylation reactions. Among these complexes, many complexes comprising a transition metal, e.g., ruthenium, palladium, and rhodium, coordinated with an optically active tertiary phosphine compound exhibit excellent catalytic performance as catalysts for enantioselective syntheses. In order to improve the catalytic performance, various phosphine compounds having a special structure have been developed to date as disclosed, e.g., in The Chemical Society of Japan (ed.), *KAGAKU SOSETSU*, Vol. 32, "YUKI KINZOKU SAKUTAI NO KAGAKU", pp. 237–238 (1982).

In particular, 2,2'-bis(diphenylphosphino)-1,1'-binaphthyl (hereinafter abbreviated as BINAP) is one of excellent phosphine compounds, and rhodium complexes and ruthenium complexes using BINAP as a ligand have been respectively reported in JP-A-55-61937 and JP-A-61-63690 (the term "JP-A" as used herein means an "unexamined published Japanese patent application").

It has also been reported that rhodium or ruthenium complexes using 2,2'-bis[di-(p-tolyl)phosphino]-1,1'-binaphthyl as a ligand bring satisfactory results in enantioselective hydrogenation and enantioselective isomerization reactions as described in JP-A-60-199898 or JP-A-61-63690. However, these known phosphine complexes have been still unsatisfactory in terms of selectivity, conversion, or duration of activity depending on the purposed reaction mode or the reaction substrate.

SUMMARY OF THE INVENTION

An object of this invention is to provide a novel phosphine compound which provides a catalyst having markedly improved catalytic performance in substrate selectivity, product selectivity, conversion, and duration of activity of various reactions.

The inventors have conducted extensive investigations on various phosphine compounds with the above object in mind. As a result, it has now been found that a phosphine compound having a lower alkyl group, a hydroxyl group, or an alkoxy group on one of naphthyl rings thereof and a diphenylphosphino group on the other naphthyl ring provides a catalyst achieving markedly improved selectivity and conversion in enantioselective syntheses. The present invention has been completed based on this finding.

The present invention relates to a novel phosphine compound, 2-substituted-2'-diphenylphosphino-1,1'-binaphthyl, represented by formula (I):

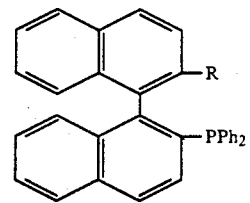

wherein Ph represents a phenyl group; and R represents a lower alkyl group or $-OR^1$, wherein $R^1$ represents a hydrogen atom, a cycloalkyl group having from 5 to 7 carbon atoms, or an alkyl group having from 1 to 6 carbon atoms which may be substituted with a halogen atom, a lower alkoxy group, a lower alkoxy group-substituted lower alkoxy group, or a phenyl group.

The present invention further relates to a novel transition metal complex having the phosphine compound represented by formula (I) as a ligand.

DETAILED DESCRIPTION OF THE INVENTION

In formula (I), the lower alkyl group as represented by R preferably has from 1 to 4 carbon atoms, and specific examples thereof include methyl, ethyl, propyl, and butyl groups. The cycloalkyl group having from 5 to 7 carbon atoms as represented by $R^1$ includes cyclopentyl and cyclohexyl groups. The alkyl group having from 1 to 6 carbon atoms which may be substituted with a halogen atom, a lower alkoxy group, or a phenyl group as represented by R includes methyl, ethyl, butyl, hexyl, isopropyl, t-butyl, fluoromethyl, 2,2,2-trifluoroethyl, 3,3,4,4,5,5,6,6,6-nonafluorohexyl, methoxymethyl, methoxyethoxymethyl, methoxypropyl, methoxybutyl, ethoxyethoxymethyl, methoxypropoxymethyl, butoxymethyl, benzyl, diphenylmethyl, and phenylpropyl groups. Preferred of these substituted or unsubstituted alkyl groups are alkyl groups having from 1 to 4 carbon atoms, a methoxymethyl group, and a methoxyethoxymethyl group. The lower alkoxy group with which the alkyl group having from 1 to 6 carbon atoms may be substituted may further have other lower alkoxy group, e.g., methoxy, ethoxy, and methoxyethoxy groups.

In formula (I), the phenyl group as represented by Ph also includes a pentafluorophenyl group.

In formula (I), R preferably represents a lower alkyl group or $-OR^1$, wherein R represents a hydrogen atom or an alkyl group having from 1 to 6 carbon atoms which may be substituted with a lower alkoxy group or a phenyl group.

The 2-substituted-2'-diphenylphosphino-1,1'-binaphthyl (I) of the present invention includes (+)- and (−)-optical isomers, and these isomers as well as the racemate thereof fall within the scope of the present invention.

The novel phosphine compound (I) wherein R is $-OR^1$ can be synthesized by, e.g., the following reaction route:

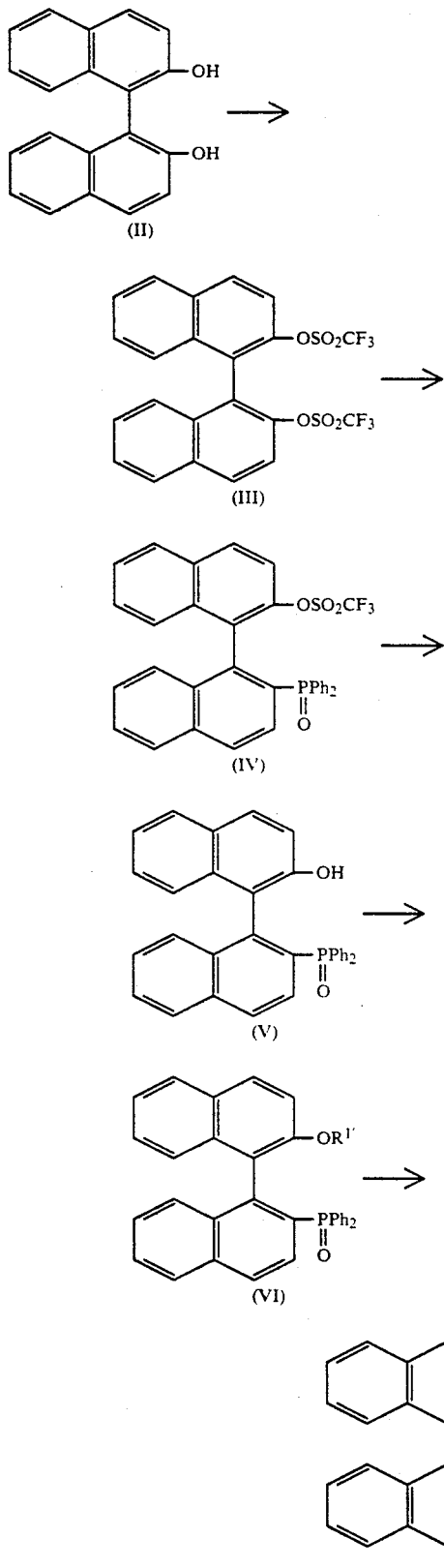

group, a lower alkoxy group-substituted lower alkoxy group, or a phenyl group.

More specifically, binaphthol (II) is reacted with trifluoromethanesulfonic acid anhydride to obtain 2,2'-bis(trifluoromethanesulfonyl)-1,1'-binaphthyl (III), which is then reacted with diphenylphosphine oxide in the presence of a palladium-phosphine complex (e.g., palladium acetate) as a catalyst to obtain 2-trifluoromethanesulfonyl-2'-diphenylphosphinoyl-1,1'-binaphthyl (IV).

The compound (IV) is saponified by using an alkali hydroxide aqueous solution and then made acidic with a hydrochloric acid aqueous solution to obtain 2-hydroxy 2'-diphenylphosphinoyl-1,1'-binaphthyl (V).

The compound (I) wherein R is —$OR^1$, wherein R is a hydrogen atom (compound (Ia)) can be obtained by treating the compound (V) with a reducing agent, e.g., trichlorosilane.

The compound (I) wherein R is —$OR^1$, wherein $R^1$ is a cycloalkyl group having from 5 to 7 carbon atoms or an alky having from 1 to 6 carbon atoms which may be substituted with a halogen atom, a lower alkoxy group, or a phenyl group (compound (Ib)) can be obtained by reacting the compound (V) with an alkylating agent to obtain a compound (VI) and treating the compound (VI) with a reducing agent, e.g., trichlorosilane.

The alkylating agent to be used in the preparation of the compound (Ib) includes cyclohexyl bromide, methyl iodide, butyl chloride, 2,2,2-trifluoroethyl iodide, 2-methoxyethoxymethyl chloride, and benzyl bromide.

The phosphine compound (I) wherein R is a lower alkyl group (compound (Ic)) can be prepared, for example, through the following reaction route:

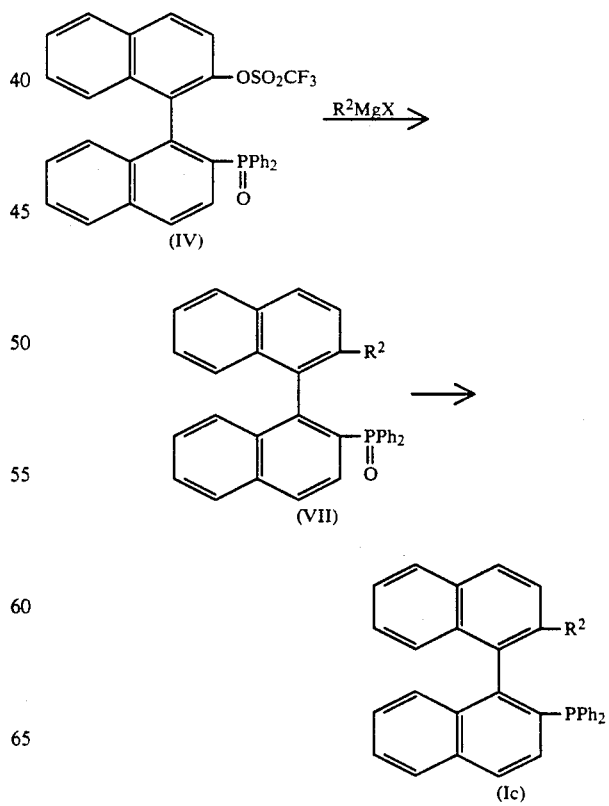

wherein Ph is as defined above; and $R^{1'}$ represents a cycloalkyl group having from 5 to 7 carbon atoms or an alkyl group having from 1 to 6 carbon atoms which may be substituted with a halogen atom, a lower alkoxy wherein Ph is as defined above; R² represents a lower alkyl group; and X represents a halogen atom.

That is, 2-trifluoromethanesulfonyl-2'-diphenylphosphinoyl-1,1'-binaphthyl (IV) prepared as described above is reacted with a lower alkylmagnesium halide (R²MgX) in the presence of a catalyst to obtain a 2-lower alkyl-2'-diphenylphosphinoyl-1,1'-binaphthyl (VII). Examples of useful catalysts include coupling catalysts, e.g., NiCl₂(dppe), wherein dppe represents 1,2-bis(diphenylphosphino)ethane.

The resulting compound (VII) is treated with a reducing agent, e.g., trichlorosilane, to obtain a 2-lower alkyl-2'-diphenylphosphino-1,1'-binaphthyl (Ic).

In the preparation of the compound (I) of the present invention, where the starting compound, binaphthol (II), is used in its optically active form, the finally obtained compound (I) is also optically active. On the other hand, where the starting binaphthol (II) is a racemate, the compound (I) is obtained in the form of a racemate. Accordingly, it is possible to obtain a desired optically active compound or a racemate depending on the end use.

The 2-substituted-2'-diphenylphosphino-1,1'-binaphthyl(I) according to the present invention serves as a ligand in the formation of complexes with transition metals. The transition metals capable of forming a complex with the compound (I) include platinum, iridium, palladium, rhodium, and ruthenium. Among them is preferred palladium. Of the transition metal complexes according to the present invention, the palladium complex, for example, can be synthesized by reacting the compound (I) with dibenzonitrile palladium dichloride according to the process disclosed in The Chemical Society of Japan (ed.), *JIKKEN KAGAKU KOZA, 4TH ED.*, Vol. 18, "YUKI KINZOKU SAKUTAI", p. 393, Maruzen (1991).

The transition metal complexes using the 2-substituted-2'-diphenylphosphino-1,1'-binaphthyl (I) as a ligand are useful catalysts for enantioselective synthesis reactions such as enantioselective silylation reaction, to produce desired reaction products in high yield at high optical purity.

Further, either the (—)-form or the (+)-form of the compound (I) can be selected as a ligand for a transition metal complex as a catalyst so as to obtain a reaction product of desired absolute configuration.

The present invention is now illustrated in greater detail with reference to Examples, but it should be understood that the present invention is not construed as being limited thereto. All the parts, percents, and ratios are by weight unless otherwise specified.

EXAMPLE 1

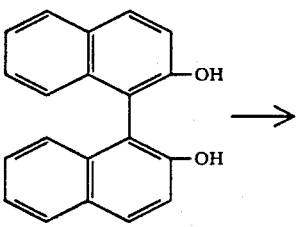
→

-continued

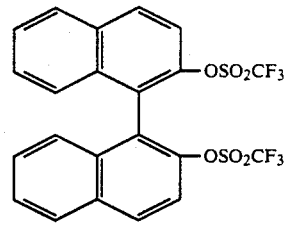

In 10 ml of methylene chloride were dissolved 1.43 g (5 mmole) of (S)-binaphthol and 1.2 ml of pyridine, and 2 ml of trifluoromethanesulfonic acid anhydride was added dropwise to the solution under ice-cooling, followed by stirring at room temperature overnight. The reaction mixture was diluted with diethyl ether and washed successively with a 5% hydrochloric acid aqueous solution and a saturated sodium chloride aqueous solution. The organic layer was filtered through a very short column of a two-layer system composed of silica gel (lower layer) and potassium carbonate (upper layer). The filtrate was concentrated under reduced pressure to obtain 2.53 g (percent yield: 92%) of (S)-2,2'-bis(trifluoromethanesulfonyl)-1,1'-binaphthyl as a colorless solid.

EXAMPLE 2

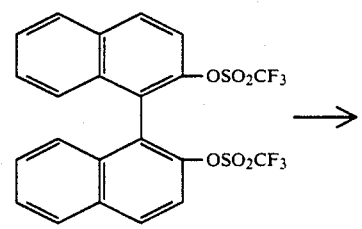
→

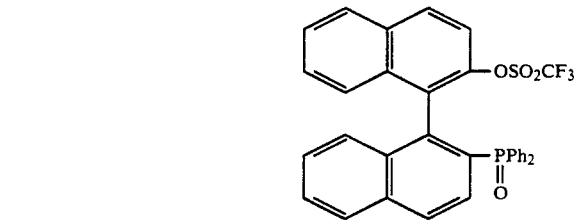

In 10 ml of dimethyl sulfoxide (DMSO) were dissolved 1.1 g (2 mmole) of the (S)-2,2'-bis(trifluoromethanesulfonyl)-1,1'-binaphthyl, 808 mg (4 mmole) of diphenylphosphine oxide, 22.5 mg (0.1 mmole) of palladium acetate, and 43 mg (0.1 mmole) of 1,4-bis(diphenylphosphino)butane (dppb) under a nitrogen atmosphere. To the solution was added 2 ml of diisopropylethylamine, and the mixture was heated at 100° C. for 12 hours with stirring. The reaction mixture was allowed to cool, diluted with ethyl acetate, and washed with water three times. The organic layer was dried over magnesium sulfate and then filtered. The filtrate was concentrated under reduced pressure, and the residue was purified by silica gel column chromatography to obtain 1.15 g (percent yield: 96%) of (S)-(—)-2-trifluoromethanesulfonyl-2'-diphenylphosphinoyl-1,1'-binaphthyl.

¹H-NMR (CDCl₃) δ: 6.9–8.1 (m, aromatic).

NMR analysis was carried out at 90 MHz using deuterated chloroform (hereinafter the same).

$^{31}$P-NMR (CDCl$_3$) δ: 28.11 (s).

IR (nujol): 1410, 1202, 1140, 895 cm$^{-1}$.

Mass (m/z): 603 (M+1), 454 (603-OTf), 201 (base peak, hereinafter abbreviated as bp) (Tf means trifluoromethanesulfonyl)

Elemental Analysis for C$_{33}$H$_{22}$O$_{22}$O$_4$F$_3$SP: Calcd (%): C 65.78; H 3.68; Found (%): C 65.65; H 3.79; [α]$^{20}_D$ −44.45° (c=0.50, CHCl$_3$)

EXAMPLE 3

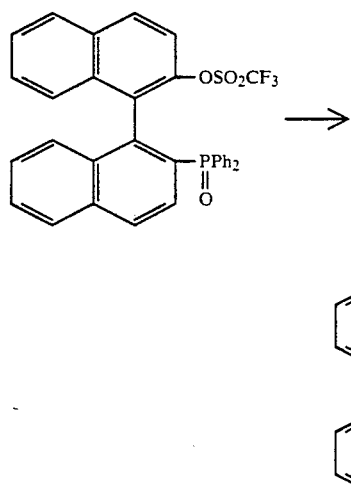

In a mixed solvent of 7 ml of 1,4-dioxane and 3.5 ml of methanol was dissolved 1.15 g of the (S)-(−)-2-trifluoromethanesulfonyl-2'-diphenylphosphinoyl-1,1'-binaphthyl obtained in Example 2, and 7 ml of a 3N sodium hydroxide aqueous solution was added thereto, followed by stirring at room temperature for 3 hours. The reaction mixture was made acidic with concentrated hydrochloric acid, diluted with ethyl acetate, washed successively with water and a sodium chloride aqueous solution, and dried over sodium sulfate. The desiccant was removed by filtration, and the filtrate was concentrated under reduced pressure. The resulting crude product was purified by silica gel column chromatography to obtain 732 mg (percent yield: 81.5%) of (S)-(+)-2-hydroxy-2'-diphenylphosphinoyl-1,1'-binaphthyl.

$^1$H-NMR: 6.3–8.2 (m).

−P-NMR 30.80 (s).

Mass (m/z): 470 (M$^+$), 268 (bp).

HR-MS for C$_{32}$H$_{23}$O$_2$P: Calcd.: 470.1436; Found: 470.1415.

Elemental Analysis for C$_{32}$H$_{23}$O$_2$P: Calcd. (%): C 81.69; H 4.93; Found (%): C 81.66; H 4.96; [α]$^{20}_D$ +110.6° (c=0.85, CH$_2$Cl$_2$).

EXAMPLE 4

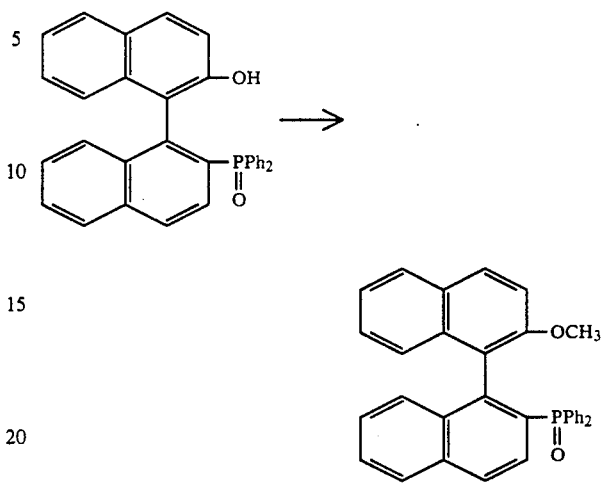

To a suspension comprising 235 mg (0.5 mole) of the (S)-(+)-2-hydroxy-2'-diphenylphosphinoyl-1,1'-binaphthy in Example 3, 276 mg (2 nmole) of potassium carbonate, and 3 ml of acetone was added 0.2 ml of methyl iodide, followed by heating at reflux for 3 hours. The reaction mixture was diluted with diethyl ether and filtered through silica gel. The filtrate was concentrated under reduced pressure to obtain 233 mg (percent yield: 96%) of (S)-(−)-2-methoxy-2'-diphenylphosphinoyl-1,1,-binaphthyl.

$^1$H-NMR: 3.58 (s, 3H), 6.75–8.05 (m, 22H).

$^{31}$P-NMR: 28.67 (s).

IR (nujol): 1590, 1250, 1105 cm$^{-1}$.

Mass (m/z): 484 (M$^{30}$), 282 (bp).

HR-MS for C$_{33}$H$_{25}$O$_2$P: Calcd.: 484.1592; Found: 484.1574.

Elemental Analysis for C$_{33}$H$_{25}$O$_2$P: Calcd. (%): C 81.80; H 5.20; Found (%): C 81.77; H 5.38; [α]$^{20}_D$ −126.9° (c=0.253, CHCl$_3$).

EXAMPLE 5

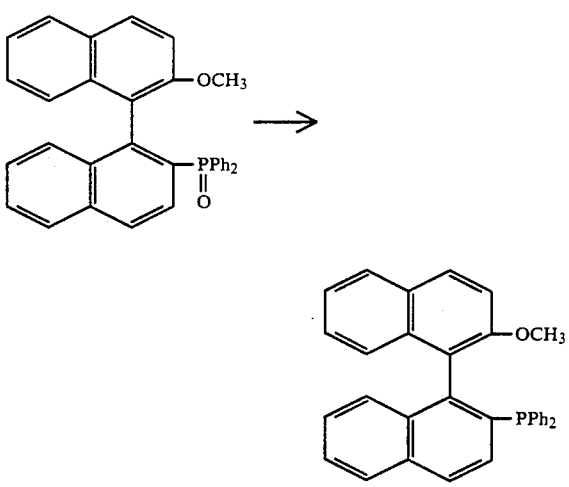

In 1 ml of xylene was dissolved 48 mg (0.1 mmole) of the (S)-(−)-2-methoxy-2'-diphenylphosphinoyl-1,1'-binaphthyl obtained in Example 4, and 0.2 ml of triethylamine and 50 ml of trichlorosilane were added thereto under a nitrogen atmosphere, followed by heating at 120° C. for 3 hours. After being allowed to cool, the reaction mixture was diluted with diethyl ether, and a small amount of a saturated sodium hydrogencarbonate aqueous solution was added thereto. The mixture was filtered through Celite, and the filtrate was dried over magnesium sulfate and concentrated. The resulting crude product was purified by silica gel column chromatography to obtain 37 mg (percent yield: 79%) of (S)-(−)-2-methoxy-2'-diphenylphosphino-1,1'-binaphthyl.

$^1$H-NMR: 3.35 (s, 3H), 6.95-8.10 (m, 22H)
IR: 1595, 1240, 1100, 1000 cm$^{-1}$.
Mass: 468 (M$^+$), 437 (bp).
HR-MS for C$_{33}$H$_{25}$OP: Calcd.: 468.1644; Found: 468.1672.
Elemental Analysis for C$_{33}$H$_{25}$OP: Calcd. (%) C 84.60; H 5.38; Found (%): C 84.61; H 5.33; $[\alpha]^{20}_D$ 94.51° (c=0.272, CHCl$_3$).

EXAMPLE 6

A reaction was carried out in the same manner as in Example 4, except for replacing the methyl iodide with benzyl bromide. The reaction mixture was filtered through Celite, and the Celite layer was washed and eluted with 10 ml of ethyl acetate. The filtrate was concentrated under reduced pressure, and the resulting crude product was purified by silica. gel column chromatography using ethyl acetate as an eluent to obtain (S)-(−)-2-benzyloxy-2'-diphenylphosphinoyl-1,1'-binaphthyl in a percent yield of 87%.

$^1$H-NMR: 4.94 (s, 2H), 6.8-8.05 (m, 27H).
$^{31}$P-NMR: 28.96 (s).
IR: 1590, 1505, 1275, 1250, 1110 cm$^{-1}$.
Mass (m/z): 560 (M$^+$), 469, 358, 201.
HR-MS for C$_{39}$H$_{29}$O$_2$P: Calcd.: 560.1905; Found: 560.1925; $[\alpha]^{20}_D$ −116.5° (c=0.11, CHCl$_3$).

EXAMPLE 7

A reaction was carried out in the same manner as in Example 5, except for using the (S)-(−)-2-benzyloxy-2'-diphenylphosphinoyl-1,1'-binaphthyl obtained in Example 6 as a starting compound, to obtain (S)-(−)-2-benzyloxy-2'-diphenylphosphino-1,1'-binaphthyl in a percent yield of 96%.

$^1$H-NMR 4.70 (d, J=13Hz, 1H), 4.95 (d, J=13 Hz, 1H), 6.77-8.03 (m, 27H).
$^{31}$P-NMR: −13.35.
IR: 1590, 1505, 1250, 1020 cm$^{-1}$.
Mass (m/z): 544 (M$^+$), 453, 437 (bp).
HR-MS for C$_{39}$H$_{29}$OP: Calcd.: 544.1956; Found: 544.1942; $[\alpha]^{20}_D$ −96.02° (c=0.12, CHCl$_3$).

EXAMPLE 8

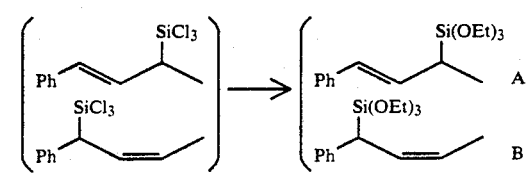

(wherein Et represents an ethyl group)

(1) A mixture of 0.01 mmole of (S)-(−)-2-methoxy-2'-diphenylphosphino-1,1'-binaphthyl, 0.92 mg (0.0025 mmole) (π-allyl)palladium chloride dimer, 325 mg (2.5 mmole) of 1-phenyl-1,3-butadiene, and 250 ml (2.5 mmole) of trichlorosilane was allowed to react at 30° C. for 12 hours under a nitrogen atmosphere. The reaction progress was traced by gas-liquid chromatography (GLC).

The reaction mixture was added to a mixture of 500 ml of ethyl alcohol and a solution of 1 ml of triethylamine in 20 ml of diethyl ether, followed by stirring for 3 hours. The reaction mixture was filtered through Celite, and the Celite layer was washed 2 or 3 times with diethyl ether. The filtrate was concentrated under reduced pressure, and the resulting oily residue was distilled under reduced pressure to obtain a 4:6 mixture of 1-phenyl-3-triethoxysilyl-1-butene (A-form) and 1-phenyl-1-triethoxysilyl-2-butene (B-form) in a 83%.

When starting with (S)-(−)-2-benzyloxy-2'-diphenylphosphino-1,1'-binaphthyl, a 1:1 mixture of A-form and B-form was obtained in a percent yield of 88%.

(2) An about 60 mg aliquot of the product was dissolved in a 1:1 (by volume) mixture of methanol and tetrahydrofuran, and 100 mg of potassium hydrogencarbonate, 58 mg of potassium fluoride, and 30 ml of a 30% hydrogen peroxide aqueous solution were added thereto, followed by stirring for 12 hours. The reaction mixture was dried over sodium sulfate, filtered, and concentrated. The residue was purified by preparative thin-layer chromatography (P-TLC) (diethyl ether/n-hexane=½ by volume) to obtain 4-phenyl-3-buten-2-ol (A'-form) and 1-phenyl-2-buten-1-ol (B'-form).

An about 10 mg aliquot each of the A'-form and B'-form was dissolved in a mixture of 0.2 ml of toluene and 0.1 ml of pyridine, and 3,5-dinitrophenyl isocyanate was added thereto, followed by allowing the mixture to react at room temperature for 3 hours. The reaction mixture was concentrated under reduced pressure, and the residue was dissolved in 1 ml of methylene chloride. Any insoluble matter was removed by filtration, and the filtrate was analyzed by high-performance liquid chromatography (HPLC) for separation of optical isomers under the following conditions to obtain the optically active compound of A'-form represented by formula:

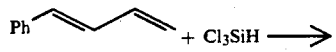

(73 %ee).

Chromatograph: LC-9A, SPD-M6A UV detector (manufactured by Shimadzu Corporation)
Column: Sumichiral OA-4000 (manufactured by Sumitomo Chemical Co., Ltd.) p0 Eluent: n-hexane/-methylene chloride/ethanol (50:15:1 by volume).

EXAMPLE 9

Compounds of A-form and B-form were obtained in the same manner as in Example 8, except for using (S)-(−)-2-benzyloxy-2'-diphenylphosphino-1,1'-binaphthyl as a catalyst (percent yield: 88%; A:B=1:1).

Similarly, the optically active compound of A'-form was obtained at an optical purity of 75 %ee.

EXAMPLE 10

Compounds of A-form and B-form were obtained in the same manner as in Example 8, except that (S)-(−)-2- benzyloxy-2'-diphenylphosphino-1,1'-binaphthyl was used as a catalyst and that the reaction was carried out at 15° C. for 12 hours and then at 30° C. for 12 hours (percent yield: 90%; A:B=1:1).

Similarly, the optically active compound of A'-form was obtained at an optical purity of 88 %ee.

EXAMPLE 11

Synthesis of (S)-(−)-2-Isopropoxy-2'-diphenylphosphinoyl-1,1'-binaphthyl (S)-(−)-2-Isopropoxy-2'-diphenylphosphinoyl-1,1'-binaphthyl was prepared in the same manner as in Example 4, except that the methyl iodide was replaced with isopropyl iodide and that the heat reflux was continued for 24 hours (percent yield: 90%).

$^1$H-NMR: 0.88 (d, J=6.0 Hz, 3H), 1.13 (d, J=6.0 Hz, 3H), 4.46 (m, 1H), 6.75–8.15 (m, 22H).

$^{31}$P-NMR 29.88 (s).

MS (m/z): 512 (M$^-$), 453, 268 (bp).

HR-MS for $C_{35}H_{29}PO_2$: Calcd.: 512.1905; Found: 512.1913.

Elemental Analysis for $C_{35}H_{29}PO_2$: Calcd. (%): C 82.01; H 5.70; Found (%): C 81.79; H 5.55; $[\alpha]^{20}_D$ 315.2° (c=0.13, CHCl$_3$).

EXAMPLE 12

Synthesis of (S)-(−)-Isopropoxy-2'-diphenylphosphino-1,1'-binaphthyl (S)-(−)-2Isopropoxy-2'-diphenylphosphino-1,1'-binaphthyl was prepared in the same manner as in Example 5, except for starting with (S)-(−)-2-isopropoxy-2'-diphenylphosphinoyl-1,1'-binaphthyl and continuing the heating for 12 hours (percent yield: 84%).

$^1$H-NMR: 0.88 (d, J=6.0 Hz, 6H), 4.48 (heptet, J=6.0 Hz, 1H), 6.75–8.05 (m, 22H).

$^{31}$P-NMR: −13.69.

MS (m/z): 496 (M$^+$), 437 (bp) HR-MS for $C_{35}H_{29}PO$: Calcd.: 496.1956; Found: 496.1942; $[\alpha]^{20}_D$ −90.0° (c=0.13, CHCl$_3$).

EXAMPLE 13

Synthesis of (S)-(−)-2-Hydroxy-2'-diphenylphosphino-1,1'-binaphthyl

In 10 ml of xylene was dissolved 470 mg of the (S)-(+)-2-hydroxy-2'-diphenylphosphinoyl-1,1'-binaphthyl obtained in Example 3 under a nitrogen atmosphere, and 1 ml of triethylamine and 0.5 ml of trichlorosilane were added thereto, followed by stirring at 100° C. for 5 hours. The reaction mixture was cooled to room temperature, diluted with diethyl ether, and washed with a 5% hydrochloric acid aqueous solution. The diethyl ether layer was dried over anhydrous sodium sulfate. The sodium sulfate was removed by filtration, and the filtrate was concentrated. The residue was purified by silica gel column chromatography (hexane:ethyl acetate=3:1 by volume) to obtain 220 mg (percent yield: 48%) of (S)-(−)-2-hydroxy-2'-diphenylphosphino-1,1'-binaphthyl.

$^1$H-NMR: 4.58 (brs, 1H), 6.65–8.00 (m, 22H, aromatic).

$^{31}$P-NMR −13.67 (s).

MS (m/z): 454 (M$^+$), 453 (M−1), 358, 268, 79 (bp).

HR-MS for $C_{32}H_{32}PO$: Calcd.: 454.1487; Found: 454.1474.

Elemental Analysis for $C_{32}H_{23}PO$: Calcd. (%): C 84.56; H 5.10; Found (%): C 84.75; H 5.27; $[\alpha]^{20}_D$ 5.011° (c=0.446, CHCl$_3$).

EXAMPLE 14

Synthesis of (S)-(−)-2-Ethyl-2'-diphenylphosphinoyl-1,1'-binaphthyl

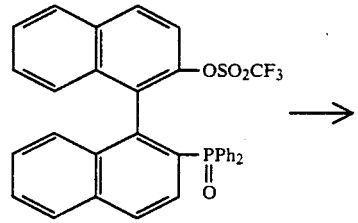

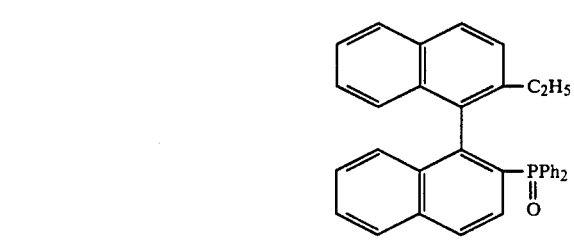

In 1 ml of ethanol were dissolved 120 mg (0.2 mmole) of 2-(trifluoromethanesulfonyl)oxy-2'-diphenylphosphinoyl binaphthyl and NiCl$_2$(dppe) (dppe means 1,2-bis(diphenylphosphino)ethane)), and 0.25 ml of a 0.9 mole/l diethyl ether solution of $C_2H_5$MgBr (0.23 mmole) was added thereto. The solution was heat refluxed for 24 hours. The reaction mixture was cooled to room temperature and diluted with diethyl ether, and a small amount of a saturated ammonium chloride aqueous solution was added thereto. The organic layer was washed with water and dried over anhydrous magnesium sulfate. The magnesium sulfate was removed by filtration, and the filtrate was concentrated under reduced pressure. The residue was purified by silica gel column chromatography (eluent: ethyl acetate) to obtain 75 mg (percent yield: 81%) of (S)-(−)-2-ethyl-2'-diphenylphosphinoyl-1,1'-binaphthyl.

$^1$H-NMR: 0.89 (t, J=6.8 Hz, 3H), 2.40 (q, J=6.8 Hz, 2H), 6.62–8.02 (m, 22H).

EXAMPLE 15

Synthesis of (S)-(−) -2-Ethyl-2'-diphenylphosphino-1,1'-binaphthyl

In 1 ml of xylene were dissolved 38 mg (0.08 mmole) of (S)-(−)-2-ethyl-2'-diphenylphosphinoyl-1,1'-binaphthyl obtained in Example 14, 73 mg (0.72 mmole) of triethylamine, and 67 mg (0.50 mmole) of trichlorosilane, and the solution was heated at 120° C. for 3 hours. The reaction mixture was worked up in a usual manner, and the resulting crude product was purified by silica gel column chromatography to obtain 29 mg (percent yield: 79%) of (S)-(−)-2-ethyl-2'-diphenylphosphino-1,1'-binaphthyl.

$^1$H-NMR: 0.82 (t, J=6.4 Hz, 3H), 2.12 (q, J=6.4 Hz, 2H), 6.65–7.96 (m, 22H) $[\alpha^{20}_D$ −85.1° (c=0.20, CHCl$_3$).

While the invention has been described in detail and with reference to specific examples thereof, it will be apparent to one skilled in the art that various changes and modifications can be made therein without departing from the spirit and scope thereof.

What is claimed is:

1. A 2-substituted-2'-diphenylphosphino-1,1'-binaphthyl represented by formula (I):

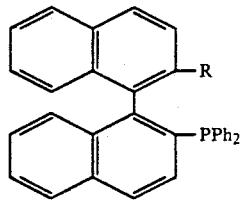

(I)

wherein Ph represents a phenyl group; and R represents —OR¹, wherein R¹ represents a hydrogen atom, a cycloalkyl group having from 5 to 7 carbon atoms, or an alkyl group having from 1 to 6 carbon atoms which may be substituted with a halogen atom, a lower alkoxy group, a lower alkoxy group-substituted lower alkoxy group, or a phenyl group.

2. A 2-substituted-2'-diphenylphosphino-1,1'-binaphthyl as in claim 1, wherein R represents —OR¹, wherein R¹ represents a hydrogen atom or an alkyl group having from 1 to 6 carbon atoms which may be substituted with a lower alkoxy group or a phenyl group.

3. A transition metal complex comprising a Group VIII transition metal and, as a ligand, a 2-substituted-2'-diphenylphosphino-1,1'-binaphthyl represented by formula (I):

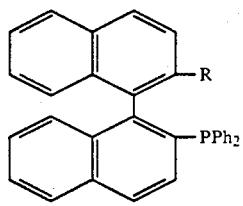

(I)

wherein Ph represents a phenyl group; and R represents —OR¹, wherein R¹ represents a hydrogen atom, a cycloalkyl group having from 5 to 7 carbon atoms, or an alkyl group having from 1 to 6 carbon atoms which may be substituted with a halogen atom, a lower alkoxy group, a lower alkoxy group-substituted lower alkoxy group, or a phenyl group.

4. A transition metal complex as in claim 3, wherein R represents —OR¹, wherein R¹ represents a hydrogen atom or an alkyl group having from 1 to 6 carbon atoms which may be substituted with a lower alkoxy group or a phenyl group.

5. A transition metal complex as in claim 3, wherein said Group VIII transition metal is platinum, iridium, palladium, rhodium, or ruthenium.

6. A transition metal complex as in claim 5, wherein said Group VIII transition metal is palladium.

7. A 2-substituted-2'-diphenylphosphino-1,1'-binaphthyl represented by formula (I):

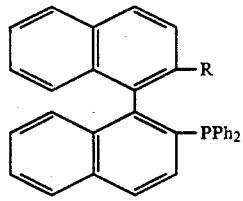

(I)

wherein Ph represents a phenyl group; and R represents a lower alkyl group.

8. A transition metal complex comprising Group VIII a transistion metal and, as a ligand, a 2-substituted-2'-diphenylphosphino-1,1'-binaphthyl represented by formula (I):

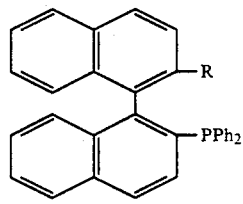

(I)

wherein Ph represents a phenyl group; and R represents a lower alkyl group.

9. A Group VIII transition metal complex as in claim 8, wherein said transition metal is platinum, iridium, palladium, rhodium, or ruthenium.

10. A Group VIII transition metal complex as in claim 9, wherein said transition metal is palladium.

* * * * *